United States Patent
Shimotsu

(10) Patent No.: US 8,270,794 B2
(45) Date of Patent: Sep. 18, 2012

(54) LIGHT GUIDE FOR ENDOSCOPES

(75) Inventor: Shinichi Shimotsu, Kanagawa-ken (JP)

(73) Assignee: Fujifilm Corporation (JP)

( * ) Notice: Subject to any disclaimer, the term of this patent is extended or adjusted under 35 U.S.C. 154(b) by 343 days.

(21) Appl. No.: 12/495,160

(22) Filed: Jun. 30, 2009

(65) Prior Publication Data

US 2009/0324184 A1   Dec. 31, 2009

(30) Foreign Application Priority Data

Jun. 30, 2008   (JP) .................. 2008-171153

(51) Int. Cl.
G02B 6/06 (2006.01)
(52) U.S. Cl. ........................................ 385/117
(58) Field of Classification Search .......... 385/117, 385/118
See application file for complete search history.

(56) References Cited

U.S. PATENT DOCUMENTS

| | | | | |
|---|---|---|---|---|
| 4,483,585 A | * | 11/1984 | Takami | 385/115 |
| 4,625,236 A | | 11/1986 | Fujimori et al. | |
| 5,513,291 A | * | 4/1996 | Buchin et al. | 385/93 |
| 2004/0081423 A1 | * | 4/2004 | Galarza | 385/146 |

FOREIGN PATENT DOCUMENTS

| | | | |
|---|---|---|---|
| JP | 56158307 A | * | 12/1981 |
| JP | S58-105202 A | | 6/1983 |
| JP | S61-41114 A | | 2/1986 |
| JP | S63-265215 A | | 11/1988 |
| JP | S64-28533 A | | 1/1989 |
| JP | H1-321407 A | | 12/1989 |
| JP | H3-277343 A | | 12/1991 |
| JP | 06-296584 A | | 10/1994 |

OTHER PUBLICATIONS

Japanese Office Action "Notice of Grounds for Rejection" dated Jul. 17, 2012; Japanese Patent Application No. 2008-171153 with translation.

* cited by examiner

*Primary Examiner* — Omar Rojas
(74) *Attorney, Agent, or Firm* — Studebaker & Brackett PC; Donald R. Studebaker

(57) ABSTRACT

The amount of heat generated at a light input portion of a light guide for endoscopes constituted by a plurality of bundled optical fibers is suppressed. The light guide for endoscopes is constituted by a plurality of bundled optical fibers, for propagating an illuminating light beam, which is focused and caused to enter a light input end facet thereof, to a light output end facet thereof, to emit the illuminating light beam onto a portion to be observed. A transparent member having a sectional shape which is at least as large as the focused spot of the illuminating light beam is provided in close contact with the light input end facets of the optical fibers. The optical fibers are connected to the transparent member in a maximally densely packed state.

15 Claims, 3 Drawing Sheets

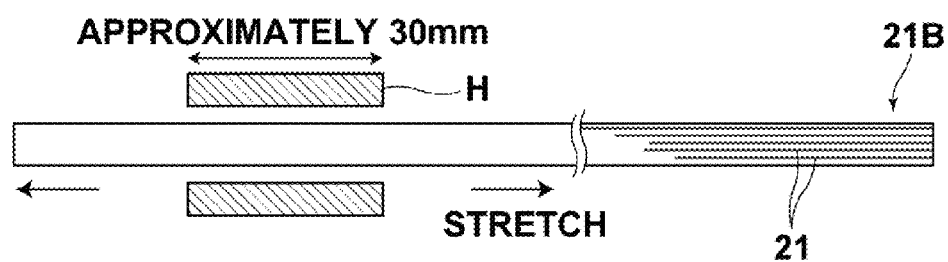
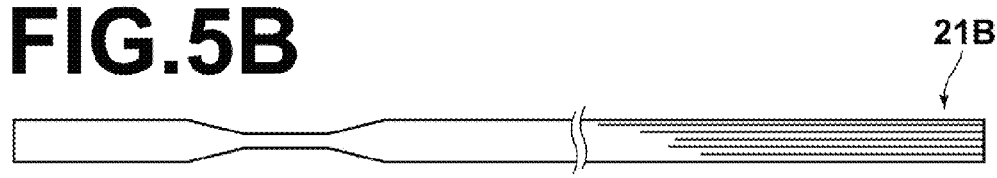
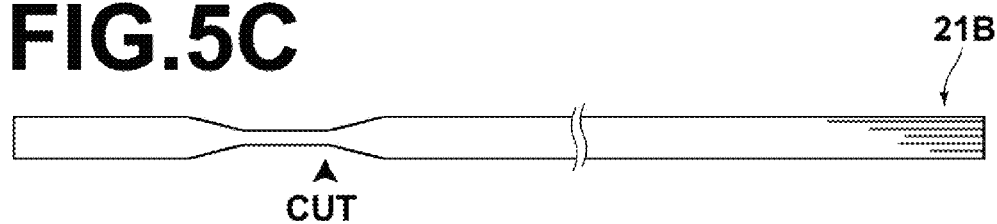

LIGHT GUIDE FOR ENDOSCOPES

BACKGROUND OF THE INVENTION

1. Field of the Invention

The present invention is related to a light guide for endoscopes, that is, a light guide that propagates light therethrough such that portions which are observed with an endoscope are illuminated.

2. Description of the Related Art

Conventionally, endoscopes are in wide use to observe and perform surgical procedures on portions within body cavities of humans. Flexible light guides for illuminating the observed portions of subjects are employed in these endoscopes. Note that in cases that surgical procedures are performed on portions, observation thereof is necessary. Therefore, portions on which surgical procedures are performed will also be referred to as "observed portions" in the present specification.

At least a portion of this type of light guide is generally constituted by a plurality of thin multi mode optical fibers which are bundled, to impart flexibility thereto. Japanese Unexamined Patent Publication No. H6 (1994)-296584 discloses an example of a light guide for endoscopes configured in this manner. This light guide for endoscopes receives illuminating light beam, by the illuminating light beam being emitted from an illuminating light source, focused, then irradiated on a first end facet of the light guide. The illuminating light beam propagates through the light guide and is emitted from a second end facet to illuminate an observed portion.

An example of a conventional light guide for endoscopes 5 is illustrated in FIG. 7. In FIG. 7, reference numeral 11 denotes a plurality of multi mode optical fibers, and reference numeral 12 denotes a filling adhesive for fixing the multi mode optical fibers 11 in a bundle so as to form a connector portion. Note that the filling adhesive 12 is generally housed within a cylindrical connector housing. Reference numeral 6 of FIG. 7 denotes an illuminating light source for emitting an illuminating light beam 7, reference numeral 8 denotes a focusing optical system for focusing the illuminating light beam 7 and causing it to enter the plurality of multi mode optical fibers 11 from a side towards first end facets (light input end facets) thereof, and reference numeral 9 denotes an optical element which is provided in close contact with the second end facets (light output end facets) of the multi mode optical fibers 11.

In light guides for endoscopes, in which the end portions that function as light input portions are constituted by a plurality of thin optical fibers as described above, there are problems that heat is easily generated at the light input portions, and that the heat degrades the optical fibers.

SUMMARY OF THE INVENTION

The present invention has been developed in view of the foregoing circumstances. It is an object of the present invention to provide a light guide for endoscopes, in which the amount of heat generated at a light input portion constituted by a plurality of bundled optical fibers is suppressed.

A light guide for endoscopes of the present invention is constituted by a plurality of bundled optical fibers, for propagating an illuminating light beam, which is focused and caused to enter a light input end facet thereof, to a light output end facet thereof, to emit the illuminating light beam onto a portion to be observed; and comprises: the plurality of optical fibers; and a transparent member having a sectional shape which is at least as large as the focused spot of the illuminating light beam, provided in close contact with the light input end facets of the optical fibers; wherein the optical fibers are connected to the transparent member in a maximally densely packed state.

Note that a glass rod, for example, may be favorably employed as the transparent member.

In the light guide for endoscopes of the present invention, it is desirable for a central optical fiber and six peripheral optical fibers which are arranged about the periphery of the central optical fiber to be employed as the plurality of optical fibers; and for the optical fibers to form the maximally densely packed state by being provided such that each of the six peripheral optical fibers is in contact with the central optical fiber, and adjacent peripheral optical fibers are in contact with each other.

In addition, it is desirable for the end portion of the optical fibers, from which the illuminating light is output, to be of a tapered shape.

Further, it is desirable for the light guide for endoscopes of the present invention to further comprise: a concave transparent member, which is provided in close contact with the light output end facet.

According to investigations conducted by the present inventor, heat generation is likely to occur at the light input portions of conventional light guides for endoscopes, which are constituted by pluralities of bundled optical fibers. The two factors described below are the cause of the heat generation. These factors will be described in detail with reference to FIG. 8.

FIG. 8 is a sectional view that schematically illustrates the light input portion of the conventional light guide for endoscopes of FIG. 7. As illustrated in FIG. 8, some of the plurality of optical fibers 11, which are fixed by the filling adhesive 12 in a bundled state, are far apart from each other, and portions of some of the optical fibers 11 are exposed outside the outer periphery of the filling adhesive 12. In the case that the plurality of optical fibers 11 are far apart from each other, the filling adhesive 12 is present in the spaces therebetween. Accordingly, an illuminating light beam which is emitted onto these spaces does not enter any optical fibers 11, but only serves to heat the filling adhesive 12. This is the aforementioned first factor that causes heat generation to occur.

As described previously, the filling adhesive 12 is generally contained within a cylindrical connector housing. Commonly, the illuminating light beam 7 is focused such that the focused spot diameter matches the outer periphery of the circle formed by the filling adhesive 12. The focused spot diameter is defined as $1/e^2$ (the diameter at the portion where the light intensity becomes $1/e^2$ of that at the center of the beam), and weak portions of the illuminating light beam 7 are emitted outside the focused spot diameter as well. For this reason, in the case that portions of the optical fibers 11 are exposed outside the outer periphery of the filling adhesive 12 as illustrated in FIG. 8, the weak portions of the illuminating light beam 7 does not efficiently enter these optical fibers 11, but rather is emitted onto and heats the end facets thereof. This is the aforementioned second factor that causes heat generation to occur.

The light guide for endoscopes of the present invention has been developed based on the above knowledge, and the transparent member having a sectional shape which is at least as large as the focused spot of the illuminating light beam may be provided in close contact with the light input end facets of the comparatively large diameter optical fibers. Therefore, heat generation at the optical fibers due to the second factor described above can be prevented. In addition, the plurality of optical fibers are in contact with the transparent member in a maximally densely packed state. Therefore, heat generation at the optical fibers due to the first factor described above can be prevented. By suppressing heat generation at the light input portions of the optical fibers in this manner, deterioration of the light input portions due to heat can be prevented.

In the light guide for endoscopes of the present invention, the end portion of the optical fibers, from which the illuminating light beam is output, may be of a tapered shape. In this case, an advantageous effect that the range which is illuminated by the illuminating light beam is increased is obtained.

Further, the light guide for endoscopes of the present invention may further comprise: the concave transparent member, which is provided in close contact with the light output end facet. In this case, the illuminating light beam which is output from the second end facet is diffused by the effect of the concave shape of the transparent member. Accordingly, an advantageous effect that the illuminated range can become even wider is obtained.

BRIEF DESCRIPTION OF THE DRAWINGS

FIGS. 5A, 5B, and 5C are diagrams for explaining a method for producing the light guide for endoscopes of FIG. 4.

DESCRIPTION OF THE PREFERRED EMBODIMENTS

Hereinafter, embodiments of the present invention will be described in detail with reference to the attached drawings.

Figure 1:
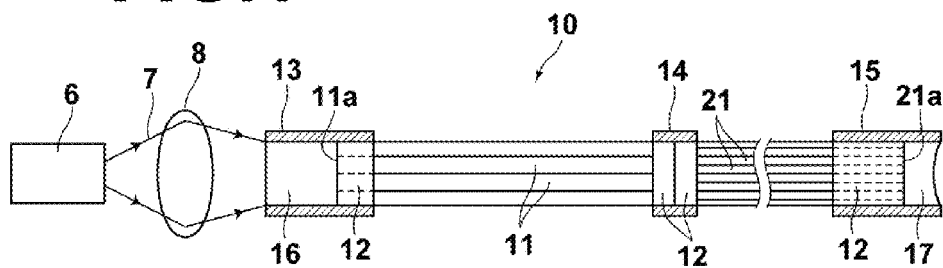
FIG. 1 is a side view that illustrates a light guide for endoscopes according to a first embodiment of the present invention.

FIG. 1 is a side view that illustrates a light guide 10 for endoscopes according to a first embodiment of the present invention. The light guide 10 for endoscopes is constituted by a plurality of bundled multi mode optical fibers 11 having comparatively large diameters, and a plurality of bundled multi mode optical fibers 21 having comparatively small diameters, connected to the multi mode optical fibers 11. A first end portion of the bundled multi mode optical fibers 11 (the left end portion in FIG. 1) and a second end portion of the bundled multi mode optical fibers 11 (the right end portion in FIG. 1) are housed in cylindrical connector housings 13 and 14, respectively, and fixed therein by filling adhesive 12. Similarly, a first end portion of the multi mode optical fibers 21 (the left end portion in FIG. 1) and a second end portion of the multi mode optical fibers 21 (the right end portion in FIG. 1) are housed in cylindrical connector housings 14 and 15, respectively, and fixed therein by filling adhesive. The light output end facets of the multi mode optical fibers 11 and the light input end facets of the multi mode optical fibers 21 are provided in close contact with each other within the central connector housing 14, thereby optically connecting the optical fibers 11 and the optical fibers 12.

A glass rod 16, which is a cylindrical transparent member, is provided in close contact with the light input end facets 11a of the multi mode optical fibers 11. The surface of the glass rod 16, which is formed by optical glass, and the surfaces of the multi mode optical fibers 11 that contact the glass rod 16 are optically polished then caused to abut each other, to be optically connected by so called optical contact. Meanwhile, a transparent member 17 having a concave shape is provided in close contact with the light output end facets 21a of the multi mode optical fibers 21.

Note that multi mode optical fibers having cladding diameters of 250 μm and core diameters of 230 μm are employed as the multi mode optical fibers 11, for example. Multi mode optical fibers having cladding diameters of 80 μm and core diameters of 60 μm are employed as the multi mode optical fibers 21, for example. A transparent member having an outer diameter of 6.5 mm and a length of 10 mm is employed as the glass rod 16.

Figure 2:
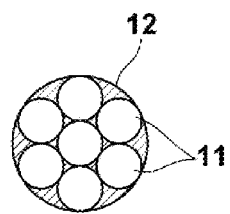
FIG. 2 is a sectional diagram that illustrates a portion of the light guide for endoscopes of FIG. 1.

Here, the state of connection between the glass rod 16 and the multi mode optical fibers 11 will be described with reference to FIG. 2. FIG. 2 is a front view of the multi mode optical fibers 11 at the portion where they connect with the glass rod 16. As illustrated in FIG. 2, seven multi mode optical fibers 11 are employed here, and six peripheral optical fibers 11 are provided around a central optical fiber 11. Each of the six peripheral optical fibers 11 is in contact with the single central optical fiber 11, and adjacent peripheral optical fibers 11 are in contact with each other. Meanwhile, the glass rod 16 is of an outer diameter that fits tightly within the cylindrical connector housing 13 that contains the filling adhesive 12. That is, the outer diameter of the glass rod 16 is equal to the outer diameter of the filling adhesive 12 (which is the inner diameter of the connector housing 13 with which the six peripheral multi mode optical fibers 11 are in contact). Therefore, the seven multi mode optical fibers 11 are connected to the glass rod 16 in a maximally densely packed state.

Figure 3:
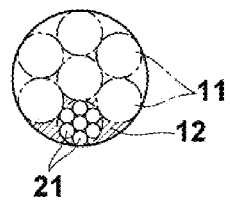
FIG. 3 is a sectional diagram that illustrates another portion of the light guide for endoscopes of FIG. 1.

Next, the state of connection among the plurality of multi mode optical fibers 11 and the plurality of multi mode optical fibers 21 will be described with reference to FIG. 3. FIG. 3 is a sectional view of the multi mode optical fibers 11 and the multi mode optical fibers 21 at the portion where they connect with each other. As illustrated in FIG. 3, seven multi mode optical fibers 21 are connected to each of the multi mode optical fibers 11, that is, a total of 49 multi mode optical fibers 21 are employed. Each group of seven multi mode optical fibers 21 are configured such that six peripheral optical fibers 21 are provided around a central optical fiber 21. Each of the six peripheral optical fibers 21 is in contact with the single central optical fiber 21, and adjacent peripheral optical fibers 21 are in contact with each other. Therefore, each group of seven multi mode optical fibers 21 is connected to each of the multi mode optical fibers 11 in a maximally densely packed state.

Figure 7:
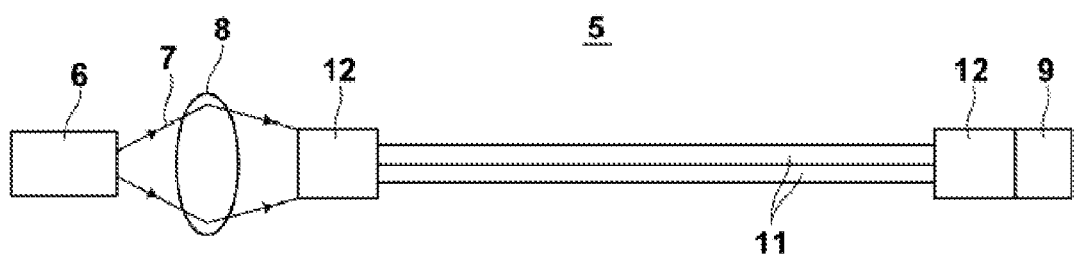
FIG. 7 is a sectional side view of a conventional light guide for endoscopes.
Figure 8:
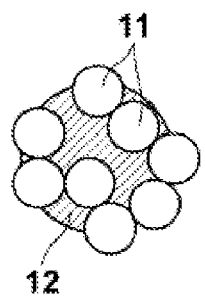
FIG. 8 is a sectional view that illustrates a portion of the conventional light guide for endoscopes of FIG. 7.

The light guide for endoscopes 10 having the construction described above is utilized in the same basic manner as the conventional light guide for endoscopes illustrated in FIG. 7. That is, the illuminating light beam 7 is emitted from the illuminating light source 6, focused by the focusing optical system 8, and is irradiated onto the end facet of the glass rod 16 in a focused state. Note that the outer diameter of the glass rod (6.5 mm) is equal to or greater than the focused spot diameter ($1/e^2$) of the illuminating light beam 7 that enters the glass rod 16.

The illuminating light 7 that enters the glass rod 16 reaches the end facets 11a of the seven multi mode optical fibers 11 either directly or after being totally reflected at the interface between the outer peripheral surface of the glass rod 16 and the connector housing 13, and enters the optical fibers 11. The illuminating light beam 7 that enters the multi mode optical fibers 11 propagates therethrough, is output from the end facets at the second end portion, and enters the 49 multi mode optical fibers 21. The illuminating light beam 7 that enters the multi mode optical fibers 21 propagates therethrough, is output from the second end facets 21a, and illuminates an observed portion within a human body cavity or the like.

In the light guide for endoscopes 10 according to the first embodiment, the outer diameter of the glass rod 16 is equal to or greater than the focused spot diameter of the illuminating light beam 7, as described above. Therefore, heat is not generated at optical fibers outside a focused region of the illuminating light beam 7, unlike in conventional light guides, in which optical fibers are positioned outside the focused spot diameter. In addition, the illuminating light beam 7 does not heat the multi mode optical fibers 11 outside the focused range thereof at the portion at which the glass rod 16 and the multi mode optical fibers 11. Accordingly, heat generation at the connection portion is also prevented.

Further, each group of seven multi mode optical fibers 21 are also connected in the maximally densely packed state. Therefore, no large gaps are formed therebetween, and heat generation due to the filling adhesive 12 within these gaps absorbing the illuminating light beam 7 can also be prevented.

In addition, the seven multi mode optical fibers 11 are connected to the glass rod 16 in the maximally densely packed state, as illustrated in FIG. 2. Therefore, heat generation due to the illuminating light beam being absorbed by the filling adhesive among the optical fibers 11 is significantly reduced. As a specific example, in the conventional light guide illustrated in FIG. 7, the amount of heat generated at the filling adhesive 12 among optical fibers 11 reaches approximately 30% of the output of the illuminating light source 6. In contrast, in the light guide of the first embodiment, the amount of heat generated at the filling adhesive 12 among optical fibers 11 can be suppressed to approximately 10% of the output of the illuminating light source 6.

Note that the portion of the light guide for endoscopes 10 close to the light output end thereof is flexed by operations of an external mechanism (not shown). In the light guide for endoscopes 10 of the first embodiment, the light output end is constituted by the comparatively small diameter multi mode optical fibers 21. Therefore, flexing operations are enabled at smaller radii of curvature. Specifically, the minimum radius of curvature at the portion of the light guide for endoscopes 10 of the first embodiment at which the plurality of multi mode optical fibers 21 are bundled is approximately 5 mm. On the other hand, the base portion of the light guide for endoscopes 10, at which flexibility is not required, is constituted by the comparatively large diameter multi mode optical fibers 11, thereby improving the durability thereof. Note that the minimum radius of curvature at the portion where the multi mode optical fibers 11 are bundled is approximately 50 mm.

Further, in the light guide for endoscopes 10 according to the first embodiment, the concave transparent member 21 is provided in close contact with the end facets 21a of the multi mode optical fibers 21. Therefore, the illuminating light beam 7 which is output from the end facets 21a is diffused by the effect of the concave shape of the transparent member 21. Accordingly, an advantageous effect that the illuminated range can become even wider is obtained.

Figure 4:
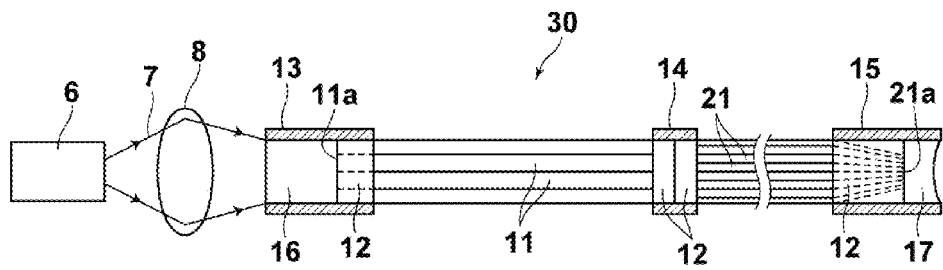
FIG. 4 is a side view that illustrates a light guide for endoscopes according to a second embodiment of the present invention.

Next, a second embodiment of the present invention will be described. FIG. 4 is a side view that illustrates a light guide for endoscopes 30 according to a second embodiment of the present invention. The light guide for endoscopes 30 differs from the light guide for endoscopes 10 of FIG. 1 in that the light output portion of the plurality of multi mode optical fibers 21 is of a tapered shape. Note that in FIG. 4, elements which are the same as those illustrated in FIG. 1 are denoted with the same reference numerals, and detailed descriptions thereof will be omitted insofar as they are not particularly necessary (the same applies to all subsequent embodiments).

A wider range of the observed portion can be illuminated by the light output portion of the plurality of multi mode optical fibers 21 being formed as tapered shapes. In multi mode fibers, there is a relationship that the product of the beam diameter (core diameter) of an input or output light beam and the angle of beam spread θ is maintained. Note that the numerical apertures of optical fibers are defined as NA=sin θ. In the light guide for endoscopes 30 according to the second embodiment, the light output portion, which are constituted by the plurality of bundled multi mode optical fibers 21. Therefore, the core diameter at the light output portion is smaller than that of the other portions. Based on the aforementioned relationship, the angle of beam spread θ at the light input portion and/or the light output portion will become greater, that is, the numerical aperture will become greater. Therefore, wider areas of observed portions can be illuminated.

In the light guide for endoscopes 30 of the second embodiment as well, the glass rod 16 is utilized at the light input portion of the light guide for endoscopes 30 in a similar manner to the light guide for endoscopes 10 of the first embodiment. Accordingly, the same advantageous effects which are obtained by the light guide for endoscopes 10 of the first embodiment are also obtained by the light guide for endoscopes 30 of the second embodiment.

Next, a method for forming the light output portions of the plurality of multi mode optical fibers 21 into the tapered shape will be described with reference to FIGS. 5A, 5B, and 5C. First, a bundle 21B, which is an assembly of a plurality of multi mode optical fibers 21, is prepared. A portion thereof is heated to 500° C. or greater, for example, by a heater H having a heating length of approximately 30 mm, and the heated portion is stretched and elongated (FIG. 5A). Thereby, the heated and stretched portion of the bundle 11B becomes tapered (FIG. 5B). Next, the bundle 21B is cut at the tapered portion (FIG. 5C). Thereby, the light output portion of the plurality of multi mode optical fibers 21B can be processed into the tapered shape described above.

Figure 6:
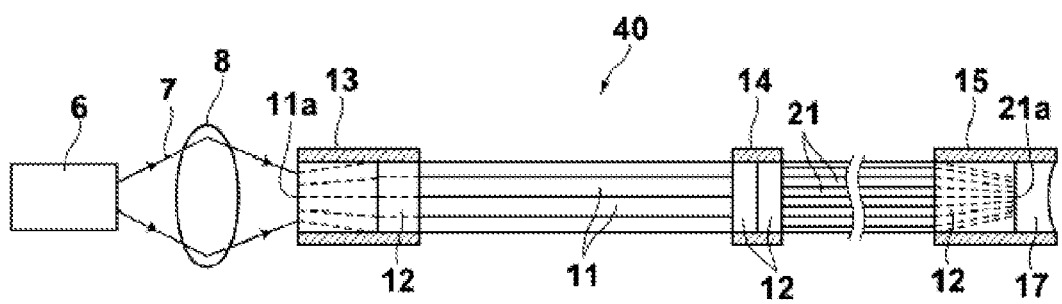
FIG. 6 is a side view that illustrates a light guide for endoscopes according to a third embodiment of the present invention.

Next, a third embodiment of the present invention will be described. FIG. 6 is a side view that illustrates a light guide for endoscopes 40 according to a third embodiment of the present invention. The light guide for endoscopes 40 differs from the light guide for endoscopes 10 illustrated in FIG. 1 in that the plurality of multi mode optical fibers 11 are omitted, and the multi mode optical fibers 21 are employed across the entirety of the length of the light guide. Accordingly, in the light guide for endoscopes 40 of the third embodiment, 49 multi mode optical fibers 21 are connected to the glass rod 16 in the manner illustrated in FIG. 3.

In the light guide for endoscopes 40 of the third embodiment as well, the glass rod 16 is utilized at the light input portion, and the plurality of multi mode optical fibers 21 are connected thereto in the manner described above. Accordingly, the same advantageous effects which are obtained by the light guide for endoscopes 10 of the first embodiment are also obtained by the light guide for endoscopes 40 of the third embodiment.

What is claimed is:

1. A light guide for endoscopes constituted by a plurality of bundled optical fibers, for propagating an illuminating light beam, which is focused and caused to enter a light input end facet thereof, to a light output end facet thereof, to emit the illuminating light beam onto a portion to be observed; the light guide comprising:

the plurality of optical fibers including bundled plural first multi mode optical fibers and bundled plural second multi mode optical fibers, each of said second multi mode optical fibers having a diameter smaller than a diameter of each of said first multi mode optical fibers; and a transparent member having a sectional shape which is at least as large as the focused spot of the illuminating light beam, provided in close contact with the light input end facets of the first multi mode optical fibers;

wherein the optical fibers are connected to the transparent member in a maximally densely packed state, and more than one of the second multi mode optical fibers are connected to each of the first multi mode optical fibers; and a central optical fiber and six peripheral optical fibers which are arranged about the periphery of the central optical fiber are employed as said bundled plural first multi mode optical fibers and as each of said second multi mode optical fibers; and the optical fibers form the maximally densely packed state by being provided such that each of the six peripheral optical fibers is in contact with the central optical fiber, and adjacent peripheral optical fibers are in contact with each other.

2. A light guide for endoscopes as defined in claim 1, wherein:

the transparent member is constituted by a glass rod.

3. A light guide for endoscopes as defined in claim 2, wherein:

a central optical fiber and six peripheral optical fibers which are arranged about the periphery of the central optical fiber are employed as said bundled plural first multi mode optical fibers and as each of said second multi mode optical fibers; and the optical fibers form the maximally densely packed state by being provided such that each of the six peripheral optical fibers is in contact with the central optical fiber, and adjacent peripheral optical fibers are in contact with each other.

4. A light guide for endoscopes as defined in claim 1, wherein:

the end portion of the optical fibers, from which the illuminating light is output, is of a tapered shape.

5. A light guide for endoscopes as defined in claim 2, wherein:

the end portion of the optical fibers, from which the illuminating light is output, is of a tapered shape.

6. A light guide for endoscopes as defined in claim 1, wherein:

the end portion of the optical fibers, from which the illuminating light is output, is of a tapered shape.

7. A light guide for endoscopes as defined in claim 3, wherein:

the end portion of the optical fibers, from which the illuminating light is output, is of a tapered shape.

8. A light guide for endoscopes as defined in claim 1, further comprising:

a concave transparent member, which is provided in close contact with the light output end facet.

9. A light guide for endoscopes as defined in claim 2, further comprising:

a concave transparent member, which is provided in close contact with the light output end facet.

10. A light guide for endoscopes as defined in claim 1, further comprising:

a concave transparent member, which is provided in close contact with the light output end facet.

11. A light guide for endoscopes as defined in claim 3, further comprising:

a concave transparent member, which is provided in close contact with the light output end facet.

12. A light guide for endoscopes as defined in claim 4, further comprising:

a concave transparent member, which is provided in close contact with the light output end facet.

13. A light guide for endoscopes as defined in claim 5, further comprising:

a concave transparent member, which is provided in close contact with the light output end facet.

14. A light guide for endoscopes as defined in claim 6, further comprising:

a concave transparent member, which is provided in close contact with the light output end facet.

15. A light guide for endoscopes as defined in claim 7, further comprising:

a concave transparent member, which is provided in close contact with the light output end facet.

* * * * *